US007504541B2

(12) United States Patent
Bodmann et al.

(10) Patent No.: US 7,504,541 B2
(45) Date of Patent: Mar. 17, 2009

(54) PROCESS FOR STABILIZING CYCLOBUTANONE DERIVATIVES

(75) Inventors: Kerstin Bodmann, Baltschieder (CH); Manuela Imig, Freigericht-Bernbach (DE); Marianne Omeis, Dorsten (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/037,992

(22) Filed: Feb. 27, 2008

(65) Prior Publication Data

US 2008/0221365 A1     Sep. 11, 2008

(30) Foreign Application Priority Data

Mar. 8, 2007     (DE) ........................ 10 2007 011 288

(51) Int. Cl.
*C07C 45/86*     (2006.01)
(52) U.S. Cl. .................................... 568/366
(58) Field of Classification Search .................. 568/366
See application file for complete search history.

(56) References Cited

U.S. PATENT DOCUMENTS 6,958,421 B2     10/2005     Bodmann et al.

FOREIGN PATENT DOCUMENTS

| EP | 0 764 625 A1 | 3/1997 |
| EP | 0 924 180 A1 | 6/1999 |
| WO | WO 02/48083 A2 | 6/2002 |

*Primary Examiner*—Sikarl A Witherspoon
(74) *Attorney, Agent, or Firm*—Oblon, Spivak, McClelland, Maier & Neustadt, P.C.

(57) ABSTRACT

A process for stabilizing cyclobutanone derivatives, comprising adding at least one of an alkali metal carbonate, alkali metal oxide, alkaline earth metal carbonate, and alkaline earth metal oxide as a stabilizer to at least one cyclobutanone derivative of the structure

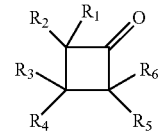

where $R_1$, $R_2$, $R_3$, $R_4$, $R_5$ and $R_6$ are each independently hydrogen or an alkyl, aralkyl, cycloalkyl, aryl, alkylaryl, hydroxyl, alkoxy, halogen, cyano or carboxyl group; and the correspondingly stabilized cyclobutanone derivatives.

15 Claims, No Drawings

PROCESS FOR STABILIZING CYCLOBUTANONE DERIVATIVES

BACKGROUND OF THE INVENTION

1. Field of the Invention

The invention relates to a process for stabilizing cyclobutanone derivatives and also to correspondingly stabilized cyclobutanone derivatives.

2. Description of the Related Art

Cyclobutanone and its derivatives are an important reactant for some preparation processes of organic compounds. The preparation of cyclobutanone is known by different processes. For example, cyclobutanone, as described in DE 101 62 456, can be obtained by rearrangement of cyclopropylmethanol in aqueous solution in the presence of an acidic heterogeneous catalyst and subsequent dehydrogenation using a heterogeneous catalyst. A further process for preparing cyclobutanone is described by DE 199 10 464; in this process, the cyclobutanone is prepared by oxidizing cyclobutanol by means of alkali metal hypochlorite or alkaline earth metal hypochlorite.

The preparation of pure cyclobutanone represents a particular challenge, since the target product is generally contaminated by reactants and by secondary components which can form both in the course of preparation and through the storage of the cyclobutanone. For example, WO 2002/48083 A2 describes numerous compounds which are detectable as impurities in aqueous cyclobutanone. These impurities are frequently colored compounds, such that contaminated cyclobutanone can be recognized by its color. For example, Eastman describes, in WO 2002/48083 and also EP 1 180 509, a purification process for crude cyclobutanone over five process stages, such that cyclobutanone can be obtained in a purity of >90%.

In spite of this complicated purification process for cyclobutanone, a deposit forms in the cyclobutanone after a few days or a few months. This precipitate is very troublesome for the use of the cyclobutanone in numerous preparation processes. In order to reduce the formation of impurities, cyclobutanone is cooled and supplied in light-protected packaging. The mechanism of decomposition of cyclobutanone is described in some publications, as listed, for example, in WO 2002/48083.

Since cyclobutanone and its derivatives serve as synthetic units for active pharmaceutical ingredient synthesis, any prevention of by-products is desirable. First, the polymerization tendency of the cyclobutanone and second, the formation of by-products should be prevented. For example, WO 2002/48083 describes the addition of phenolic compounds to cyclobutanone and derivatives thereof, which are distributed homogeneously in the product, in order to prevent the formation of by-products by transport and storage. These phenolic compounds are the classical phenol-based stabilizers—so-called sterically hindered phenols, for example 2,6-di-tert-butyl-4-methylphenol, also known by the abbreviation BHT.

It is thus an object of the present invention to provide a process for stabilizing cyclobutanone derivatives. In particular, the stabilizer added should also be removable again from the cyclobutanone derivative, in order that the stabilizer itself does not cause problems in the further active pharmaceutical ingredient synthesis. Moreover, the stabilizer used should be non-toxic.

SUMMARY OF THE INVENTION

It has been found that, surprisingly, even stabilizers undissolved in the cyclobutanone derivative can provide sufficient stabilization. For example, even the addition of 2% by weight of sodium carbonate or calcium oxide leads to storage stability of cyclobutanone over several weeks. The present invention has the advantage over the prior art that this stabilizer is present in undissolved form in the product and can thus be removed easily from the product by filtration. Moreover, the stabilizers used in the process according to the invention are non-toxic substances which are additionally inexpensive.

The invention thus provides a process for stabilizing cyclobutanone derivatives, comprising adding at least one of an alkali metal carbonate, alkali metal oxide, alkaline earth metal carbonate, and alkaline earth metal oxide as a stabilizer to at least one cyclobutanone derivative of the structure

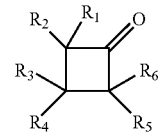

where $R_1$, $R_2$, $R_3$, $R_4$, $R_5$ and $R_6$ are each independently hydrogen or an alkyl, aralkyl, cycloalkyl, aryl, alkylaryl, hydroxyl, alkoxy, halogen, cyano or carboxyl group.

This invention further provides a stabilized cyclobutanone derivative, comprising a cyclobutanone derivative of the structure

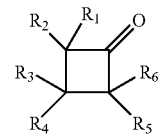

where $R_1$, $R_2$, $R_3$, $R_4$, $R_5$ and $R_6$ are each independently hydrogen or an alkyl, aralkyl, cycloalkyl, aryl, alkylaryl, hydroxyl, alkoxy, halogen, cyano or carboxyl group, and at least one of an alkali metal carbonate, alkali metal oxide, alkaline earth metal carbonate, and alkaline earth metal oxide as a stabilizer.

DETAILED DESCRIPTION OF THE INVENTION

The invention is a process for stabilizing cyclobutanone derivatives, comprising adding at least one of an alkali metal carbonate, alkali metal oxide, alkaline earth metal carbonate, and alkaline earth metal oxide as a stabilizer to at least one cyclobutanone derivative of the structure 1

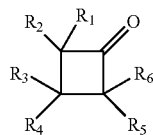 (1)

where $R_1$, $R_2$, $R_3$, $R_4$, $R_5$ and $R_6$ are each independently hydrogen or an alkyl, aralkyl, cycloalkyl, aryl, alkylaryl, hydroxyl, alkoxy, halogen, cyano or carboxyl group.

In the process according to the invention, preference is given to using a cyclobutanone derivative which comprises hydrogen as substituents of the $R_1$ to $R_6$ type. In a particular embodiment of the process according to the invention, a mixture of different cyclobutanone derivatives may be used.

In the process according to the invention, preference is given to using alkali metal and alkaline earth metal carbonates selected from potassium carbonate and sodium carbonate, or alkali metal and alkaline earth metal oxides selected from magnesium oxide and calcium oxide, as the stabilizer. Preference is given to adding sodium carbonate to the cyclobutanone derivative in the process according to the invention. A mixture of different alkali metal and alkaline earth metal carbonates or a mixture of different alkali metal and alkaline earth metal oxides may be used as the stabilizer. A mixture of carbonates and oxides of the alkali metals and/or alkaline earth metals may be used as the stabilizer.

The stabilizer—which means the carbonates and oxides of the alkali metals and alkaline earth metals—is added to the cyclobutanone derivative preferably in a total amount of 0.1 to 5% by weight, preferably of 0.5 to 3% by weight, based on the cyclobutanone derivative, in the process according to the invention.

The stabilizer is advantageously added in the process according to the invention as a solid. Since the stabilizer used in the process according to the invention does not dissolve in the cyclobutanone derivative, simple removal of the stabilizer just before the cyclobutanone derivative is used as a reactant in a preparation process is thus possible, for example by filtration or decantation.

The stabilizer is added in the process according to the invention preferably at a temperature of 20 to 30° C., preferentially at a temperature of 20.5 to 24° C. and more preferably at room temperature.

It is advantageous in the process according to the invention to add the stabilizer immediately after the last process stage of the workup, in order that as far as possible no undesired by-products have already formed before the addition of the stabilizer. Preference is given to adding the stabilizer immediately after distillation of the cyclobutanone derivatives.

The invention is also a stabilized cyclobutanone derivative, comprising a cyclobutanone derivative of the structure 1 and at least one of an alkali metal carbonate, alkali metal oxide, alkaline earth metal carbonate, and alkaline earth metal oxide as a stabilizer.

The inventive stabilized cyclobutanone derivative preferably comprises a cyclobutanone derivative which comprises hydrogen as substituents of the $R_1$ to $R_6$ type. In a particular embodiment of the inventive stabilized cyclobutanone derivative, it may also comprise a mixture of different cyclobutanone derivatives.

The inventive stabilized cyclobutanone derivative preferably comprises alkali metal and alkaline earth metal carbonates selected from potassium carbonate and sodium carbonate, or alkali metal and alkaline earth metal oxides selected from magnesium oxide and calcium oxide, as the stabilizer. The inventive stabilized cyclobutanone derivative preferably comprises sodium carbonate as the stabilizer. The inventive stabilized cyclobutanone derivative may comprise either a mixture of different alkali metal and alkaline earth metal carbonates or a mixture of different alkali metal and alkaline earth metal oxides as the stabilizer. A mixture of carbonates and oxides of the alkali metals and/or alkaline earth metals may also be possessed by the inventive stabilized cyclobutanone derivatives as the stabilizer.

The inventive stabilized cyclobutanone derivative comprises the stabilizer—i.e. the carbonates and oxides of the alkali metals and alkaline earth metals—in a total amount of 0.1 to 5% by weight, preferably of 0.5 to 3% by weight, based on the cyclobutanone derivative.

The stabilizer is present in the inventive stabilized cyclobutanone derivative predominantly as a solid; in particular, the carbonates and also the oxides of the alkali metals and alkaline earth metals are present as a sediment or else in the form of a suspension.

The inventive stabilized cyclobutanone derivative can be prepared by the process according to the invention.

The examples which follow are intended to illustrate the inventive stabilized cyclobutanone derivative and also its preparation in detail, without any intention that the invention be restricted to this embodiment.

EXAMPLES 5 g of cyclobutanone are weighed in a snap-lid glass bottle and admixed with in each case 0.1 g of the stabilizer to be tested. The storage is effected at room temperature. The purity is checked by a gas chromatography analysis (column: 30 m DB-WAX, ID 0.25 mm, FD 0.25µ; isothermal 50° C. 6 min./10° C./min. to 250° C.; the evaluation is in area %, GC area %). Before the gas chromatography analysis, the samples are diluted with diethyl ether in a ratio of cyclobutanone to diethyl ether of 1:2 (based on weight).

| Storage time (in days) | Without stabilizer (content of cyclobutanone in GC area %) | CaO (content of cyclobutanone in GC area %) | $Na_2CO_3$ (content of cyclobutanone in GC area %) | $K_2CO_3$ (content of cyclobutanone in GC area %) | 2,2,6,6-tetramethyl-piperidine (content of cyclobutanone in GC area %) |
|---|---|---|---|---|---|
| 0 | 98.70 | 98.70 | 98.70 | 98.70 | 98.70 |
| 28 | 97.27 | 97.28 | 98.08 | 95.90 | 97.76 |

| Storage time (in days) | Without stabilizer (content of cyclobutanone in GC area %) | CaO (content of cyclobutanone in GC area %) | $Na_2CO_3$ (content of cyclobutanone in GC area %) | $K_2CO_3$ (content of cyclobutanone in GC area %) | 2,2,6,6-tetra-methyl-piperidine (content of cyclobutanone in GC area %) |
|---|---|---|---|---|---|
| 42 | 95.43 | 95.21 | 96.65 | 96.24 | 96.80 |
| 49 | 95.06 | 95.98 | 95.93 | 94.89 | 95.63 |

2,2,6,6-Tetramethylpiperidine is likewise a stabilizer, but is in practice ruled out for use as a stabilizer for cyclobutanone owing to its toxicity.

The disclosure of DE 102007011288.4, filed Mar. 8, 2007, is hereby incorporated by reference.

The invention claimed is:

1. A process for stabilizing cyclobutanone derivatives, comprising adding at least one of an alkali metal carbonate, alkali metal oxide, alkaline earth metal carbonate, and alkaline earth metal oxide as a stabilizer to at least one cyclobutanone derivative of the structure

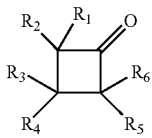

where $R_1$, $R_2$, $R_3$, $R_4$, $R_5$ and $R_6$ are each independently hydrogen or an alkyl, aralkyl, cycloalkyl, aryl, alkylaryl, hydroxyl, alkoxy, halogen, cyano or carboxyl group.

2. A process according to claim 1, wherein the stabilizer comprises at least one of potassium carbonate, sodium carbonate, magnesium oxide and calcium oxide.

3. A process according to claim 1, wherein the stabilizer comprises sodium carbonate.

4. A process according to claim 1, wherein the stabilizer is added to the cyclobutanone derivative in an amount of 0.1 to 5% by weight based on the cyclobutanone derivative.

5. A process according to claim 1, wherein the stabilizer is added as a solid.

6. A process according to claim 1, wherein the stabilizer is added to the cyclobutanone derivative in an amount of 0.5 to 3% by weight based on the cyclobutanone derivative.

7. A process according to claim 1, wherein the stabilizer is added at a temperature of 20 to 30° C.

8. A process according to claim 1, wherein $R_1$, $R_2$, $R_3$, $R_4$, $R_5$ and $R_6$ are each hydrogen.

9. A stabilized cyclobutanone composition, comprising at least one cyclobutanone derivative of the structure

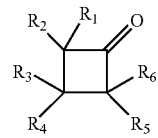

where $R_1$, $R_2$, $R_3$, $R_4$, $R_5$ and $R_6$ are each independently hydrogen or an alkyl, aralkyl, cycloalkyl, aryl, alkylaryl, hydroxyl, alkoxy, halogen, cyano or carboxyl group, and at least one of an alkali metal carbonate, alkali metal oxide, alkaline earth metal carbonate, and alkaline earth metal oxide as a stabilizer.

10. A stabilized cyclobutanone composition according to claim 9, wherein the composition comprises at least one of potassium carbonate, sodium carbonate, magnesium oxide and calcium oxide.

11. A stabilized cyclobutanone composition according to claim 9, wherein the composition comprises sodium carbonate.

12. A stabilized cyclobutanone composition according to claim 9, wherein the stabilizer is present in an amount of 0.1 to 5% by weight based on the cyclobutanone derivative.

13. A stabilized cyclobutanone composition according to claim 9, wherein the stabilizer is present as a solid.

14. A stabilized cyclobutanone composition according to claim 9, wherein the stabilizer is present in an amount of 0.5 to 3% by weight based on the cyclobutanone derivative.

15. A stabilized cyclobutanone composition according to claim 9, wherein $R_1$, $R_2$, $R_3$, $R_4$, $R_5$ and $R_6$ are each hydrogen.

* * * * *